United States Patent [19]

MacGregor

[11] 4,101,984

[45] Jul. 25, 1978

[54] CARDIOVASCULAR PROSTHETIC DEVICES AND IMPLANTS WITH POROUS SYSTEMS

[76] Inventor: David C. MacGregor, 81 Wimbleton Rd., Islington, Ontario, Canada

[21] Appl. No.: 683,382

[22] Filed: May 5, 1976

[30] Foreign Application Priority Data

May 9, 1975 [CA] Canada .................................. 226993
Dec. 22, 1975 [GB] United Kingdom ............... 52474/75

[51] Int. Cl.$^2$ ........................... A61F 1/22; A61F 1/24
[52] U.S. Cl. ................................................. 3/1.5; 3/1;
3/1.4; 3/1.7; 128/1 D; 128/92 C; 128/419 P; 427/2
[58] Field of Search ........................... 3/1.5, 1.7, 1.4, 1, 3/1.9; 128/92 C

[56] References Cited

U.S. PATENT DOCUMENTS

| 3,689,942 | 9/1972 | Rapp ......................................... 3/1.5 |
| 3,855,638 | 12/1974 | Pilliar ......................................... 3/1 |
| 3,914,802 | 10/1975 | Reick ......................................... 3/1.4 |
| 4,017,911 | 4/1977 | Kafesjian et al. ........................... 3/1.5 |

OTHER PUBLICATIONS

"An Experimental Study of the Use of Polyvinyl Sponge for Aortic Grafts" by N.E. Shumway et al., Surgery, Gynecology & Obstetrics, Jun. 1955, pp. 703–706.

"Porous Segmented Polyurethanes–Possible Candidates as Biomaterials" by Garth L. Wilkes et al., Journal of Biomedical Materials Research, vol. 7, No. 6, Nov. 1973, pp. 541–554.

"Aortic Valve Prosthesis," The Bulletin of the Dow Corning Center for Aid to Medical Research, vol. 1, No. 1, Oct. 1959.

Primary Examiner—Ronald L. Frinks
Attorney, Agent, or Firm—Sim & McBurney

[57] ABSTRACT

A novel cardiovascular prosthetic device or implant having many useful cardiovascular applications comprises a porous surface and a network of interconnected interstitial pores below the surface in fluid flow communication with the surface pores. Tissue forms a smooth thin adherent coating of self-determining thickness on the porous surface making it resistant to the formation of the blood clots normally associated with the presence of foreign bodies in the blood stream.

6 Claims, 10 Drawing Figures

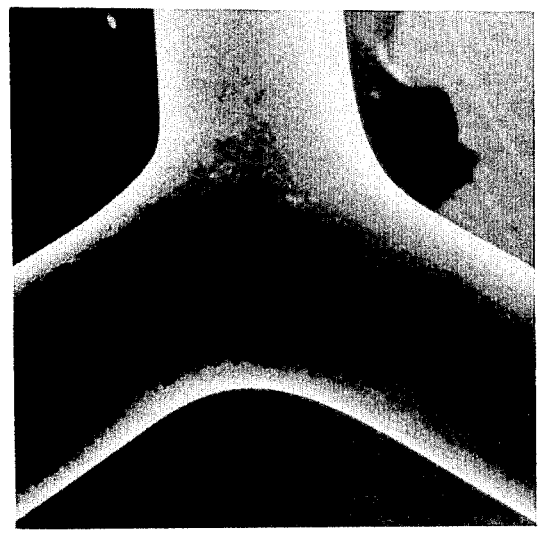
FIG. 1
FIG. 2
FIG. 3
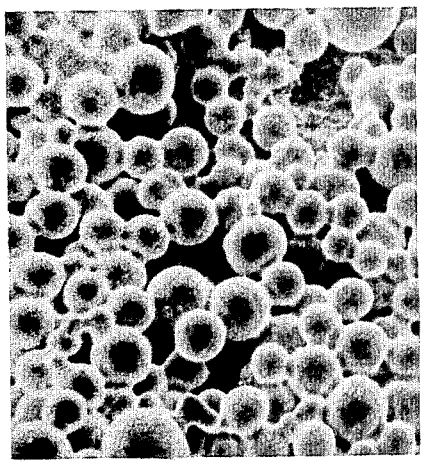
FIG. 4

CARDIOVASCULAR PROSTHETIC DEVICES AND IMPLANTS WITH POROUS SYSTEMS

FIELD OF INVENTION

This invention relates to novel prosthetic devices and implants for cardiovascular use.

BACKGROUND OF THE INVENTION

It is well known that the introduction of foreign bodies into the blood stream, for example, the polished metal surfaces of artificial heart valves, tends to cause the formation of blood clots which may break loose and embolize to various parts of the body. Such thromboembolic problems have led to the administration of anticoagulants to patients with artificial heart valves. The effects of these anticoagulants on the blood clotting mechanism cause difficulties in stopping the flow of blood through even a minor flesh wound. In addition, flexible plastic conduits are used for vascular graft purposes and such surfaces also are thrombogenic.

Attempts have been made to overcome the thromboembolic problems of polished metal heart valves by providing a porous fabric covering over blood-engaging metal parts. When such porous fabrics have been used for covering metal heart valve parts, pores of typical size 500 to 700 microns have been provided and some tissue ingrowth has been observed. While the fabric covering has resulted in a decreased incidence of thromboembolism, apparently due to the observed tissue ingrowth, such valves do suffer from other defects, notably wear of the fabric, causing cloth fragment embolism and chronic hemolytic anemia as a result of turbulence of the blood over disrupted fabric coverings.

To date, the prior art has been unable to provide a heart valve which not only overcomes the thromboembolic problems of a smooth metal surface but also does not exhibit the wear failure problem of the prior art fabric covered heart valves.

SUMMARY OF THE INVENTION

The present invention provides a heart valve which overcomes the prior art defects by providing the blood-engaging metallic parts in the form of a solid substrate having an adherent porous metallic surface coating which has a network of interconnected pores therein. It has been found that the rigid nature of the metal coating, the strength of the substrate-coating interface and the strength of the particle-particle bond in the coating provide excellent strength and wear resistance characteristics while nucleated cells circulating in the blood stream colonize onto the blood-engaging surface of the porous coating and subsequently differentiate into other cell types to form a thin, smooth, generally uniformly-thick, firmly attached tissue covering on the surface. The tissue covering is formed rapidly over about a one month period, does not appear to increase significantly in thickness thereafter, and includes flattened endothelial-like cells at the surface thereof. The tissue formation is not accompanied by thrombosis or embolish owing to its blood-compatible nature, and once the maximum thickness has been attained, the tissue covering is self-regenerating.

BRIEF DESCRIPTION OF DRAWINGS

FIG. 1 is a photograph of uncoated metal strut members of a heart valve cage at 25 times magnification;

FIG. 2 is a photograph of the strut members in FIG. 1 coated with −500 mesh metallic powder at 25 times magnification;

FIG. 3 is a close-up photograph of the surface of the coating of FIG. 2 at 750 times magnification;

FIG. 4 is a close-up photograph of the surface of the coating of FIG. 2 at 3500 times magnification;

GENERAL DESCRIPTION OF INVENTION

Figure 5:
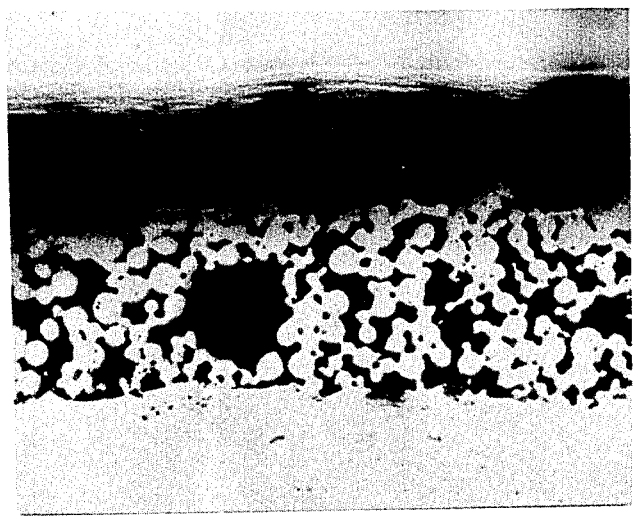
FIG. 5 is a thin section taken through a porous coated metal heart valve element after positioning in the blood stream of a dog for 2 months at 300 times magnification showing the formation and ingrowth of smooth-surfaced endothelialized tissue on the porous surface.

In U.S. Pat. No. 3,855,638, there is described a surgical prosthetic device consisting of a metal substrate with a porous metal coating into which bone tissue may grow for incorporation of the prosthesis into the body. The porous coating used in this prior art device has several essential requirements, including restrictions on coating thickness, interstitial pore size and coating porosity. These parameters are dictated by the strength requirements of the surgical prosthetic device, namely, that the coating and the coating-substrate interface have strengths at least that of bone, so that there is no danger of failure of the prosthesis after ingrowth of bone tissue.

In cardiovascular uses, however, strength is a less important consideration, and the ranges of parameters chosen are dictated to some degree by the intended use of the prosthetic device or implant.

Further, the mechanism of incorporation of the surgical prosthetic device of this prior art into the body is by ingrowth of tissue into the coating while the present invention involves quite a different mechanism which arises from the different environment of the devices of the invention as compared with that of the prior art.

Heart valves include a plurality of components including an occluder, typically a ball or disc, an occluder seating ring, occluder guide struts, muscle guards to prevent interference by muscle with movement of the occluder and a sewing ring to attach the valve to the heart. The occluder seating ring, occluder guide struts and muscle guards usually are constructed of metal. The occluder may be metal or other material.

In accordance with this invention, the engaging elements of a heart valve are formed as composites having a dense coherent metallic substrate and a rigid metallic porous coating which is adhered to the substrate and consists of metallic particles joined to adjacent particles to form an interconnected network of pores which is substantially uniformly distributed throughout the coating. It may be desirable to omit such coating from substrate surfaces where there is relative movement between members. It is preferred to form the coating from fine metallic particles, typically of −500 mesh size, in order to minimize abrasion between heart valve elements and hemolysis of the blood. It has been found that porous coatings formed from finer particles provide smoother tissue coatings than porous coatings formed from coarser particles.

It is also preferred to provide a thin porous coating on the metal substrate surfaces in order to provide the maximum orifice for blood flow, and typically the thickness is about 20 to 300 microns, preferably about 50 to about 150 microns.

The shear strength of the composite surface is important, especially where heart valve surfaces are in relative motion, and it is necessary that the composite have a high fatique tolerance, the endurance limit ($10^7$ cycles) being greater than 500 psi. It is preferred for the surface coating interface and the coating itself to have shear strengths greater than about 1000 psi, more particularly greater than about 3000 psi.

The porosity of the coating portion of the composite varies between about 10 and about 50%.

The invention is not restricted to heart valves but is applicable to a wide variety of cardiovascular prosthetic devices or implants having blood engaging surfaces. In accordance with the invention, the blood engaging surface is porous in nature and has an interconnected network of pores in the subsurface thereof.

The cardiovascular phosthetic devices or implants used in the present invention may be, in some cases, as in the heart valve case as mentioned above, in the form of a porous coating on a coherent substrate, with the network of interconnected pores extending throughout the coating only. Alternatively, the prosthetic device or implant may be wholly porous with the network of interconnected pores extending throughout the body of the device.

An example of the use of the latter type of device is as the metal electrode tip of a heart pacemaker, although the electrode tip also may be provided in the composite form, if desired.

The pacemaker electrode tip and the heart valves use metal as the material of construction. The term "metal" as used herein is intended to include metal alloys. The metal utilized is one which is non toxic to the blood and body tissue. One such material is the cobalt alloy that is known by the trade mark "VITALLIUM".

Where such metal prosthetic devices and implants are of the composite type, they may be formed by a number of techniques involving sintering, the particular sintering procedure depending to some extent on the size of the particles from which the porous coating is formed.

The metal particles from which the porous coating is formed generally fall into one of four categories, namely −500 mesh (less than about 20μ, −325 + 500 mesh (about 20 to about 50μ, −100 + 325 mesh (about 50 to about 200μ and +100 mesh (greater than about +200μ. The term "mesh" used herein refers to the U.S. Standard Sieve mesh size.

In each case, the smooth coherent substrate is first roughened, for example, by blasting with abrasive material.

The coating of metal particles then is formed on the roughened surface. The metal in the substrate and coating usually are the same, but different metals may be used.

In one procedure, a binder for the metal particles first is sprayed onto the roughened metal surface and the device then is suspended in a fluidized bed of powder metal particles to form a coating on the roughened surface. The coated body is withdrawn from the fluidized bed and the binder allowed to dry. This procedure has been found to be satisfactory for each of the particle sizes, except for the −500 mesh particles.

In an alternative procedure, the powder metal particles are mixed with a binder to form a fairly viscous slurry which is spray applied to the roughened surface to form the coating thereon, the coating thereafter being dried. It has been found that this procedure is satisfactory for −325 mesh size particles and below.

In a further procedure, the metal particles and binder are slurried and the roughened surface is dipped into the slurry. Excess material is allowed to run off and the coated body is dried.

In each case, the preform of dried coating and substrate is sintered to cause metal fusion interconnection of the metal particles one with another and with the roughened substrate surface to provide a rigid porous structure having a network of interconnected pores substantially uniformly distributed throughout the coating.

It is possible to build up any desired thickness of porous coating on the coherent substrate by presintering the dried coating to provide some strength thereto and then repeat the coating and presintering operation for as many cycles as is required to build up the desired thickness. When the desired thickness has been achieved, the composite is sintered to provide the required particle-particle and particle-substrate adhesions.

The presintering and sintering temperatures which are preferably utilized depend on the particle size of the metal particles, lower temperatures generally being used for smaller particle sizes.

Thus, for −500 mesh metal particles, presintering preferably is carried out by heating at a temperature of about 2000° F (about 1100° C) momentarily or up to about 10 minutes and then cooling while sintering preferably is carried out by heating at a temperature of about 2150° F (about 1175° C) for about 60 to about 90 minutes in a hydrogen or other reducing gas atmosphere, or under vacuum.

For the −325 +500 mesh metal particles, presintering preferably is carried out by heating at a temperature of about 2100° F (about 1150° C) for about 8 minutes, while sintering preferably is carried out by heating at a temperature of about 2200° F (about 1200° C) for about 60 to about 90 minutes in a hydrogen or other reducing gas atmosphere, or under vacuum.

When metal particles of particle size +325 mesh are used, the presintering preferably is carried out at a temperature of about 2200° F (about 1200° C) and sintering preferably is carried out at a temperature of about 2200° to about 2300° F (about 1200° C to about 1250° C) for about 2 to about 3 hours, in a hydrogen or other reducing gas atmosphere, or under vacuum.

Following formation of the porous coating, it may be machined and refined, if desired, to improve its surface characteristics.

The metal particles generally are substantially spherical, although other geometrical shapes and mixtures of shapes may be used. FIGS. 1 to 4 illustrate part of a typical device provided in accordance with this invention wherein the coating is formed from −500 mesh metal particles.

Thus, the normal polished metal surface struts (FIG. 1) of a heart valve cage, the apex of which is seen in FIGS. 1 and 2, is coated with an adhered rigid porous coating of substantially spherical metal particles, giving the struts the appearance seen in FIG. 2. In the highly magnified photographs of FIGS. 3 and 4, it can be seen that the metal particles are adhered one to another by diffusion bonded regions to define a plurality of surface pores. The surface pores communicate with a subsurface interconnected network of interstitial pores, as may be seen from the thin section of FIG. 5.

Wholly porous metallic devices may be formed by sintering the metal particles in a mold at the sinter temperatures specified above for the porous coatings. Binders may be used, if necessary.

The present invention is not limited to metal as the material of construction of the prosthetic device or implant and many other constructional materials inert to blood may by used, either alone or in combinations of two or more such materials, provided that they can be provided in a porous form. Typical materials include flexible or rigid plastics, ceramics and carbon.

When plastic materials are used in this invention, they may be provided in rigid form or in flexible form and in wholly porous or composite form. The rigid plastics may be used in similar applications to the rigid metal bodies, as outlined below. The flexible plastic materials, however, have particular utilities not enjoyed by the metal bodies owing to the rigid nature of the metal bodies.

One method of forming a porous polymer structure involves pulverizing the polymer to the required particle size and then compressing the polymer powder at pressures below about 100 psi and at a temperature in the range of about 20° to about 100° F (about 7° to about 38° C).

Another method of formation of porous structures for use in the present invention is to blend together a moldable flexible polymeric material and solvent-elutable particles in quantities to provide a continuous phase of polymer and a dispersed phase of solvent-elutable particles in the blend. The blend may be subjected to compression molding to the desired shape, if desired. The resultant body then is contacted with solvent to remove the solvent-elutable particles to leave an open network of interconnected pores throughout the body.

The solvent-elutable particles and the elution solvent should be non-toxic in nature so that any residual material is not harmful to body tissues or blood in use. Typically, the solvent elutable particles are water-soluble, for example, sodium chloride or sodium carbonate particles.

The particle size of the particles to a large degree dictates the pore size in the polymer body, although irregular shapes generally result.

The pore size, volume and shape in the product may be controlled by varying the size, shape and distribution of the solvent-elutable particles and the weight ratio of the polymer to particles.

Figure 7:
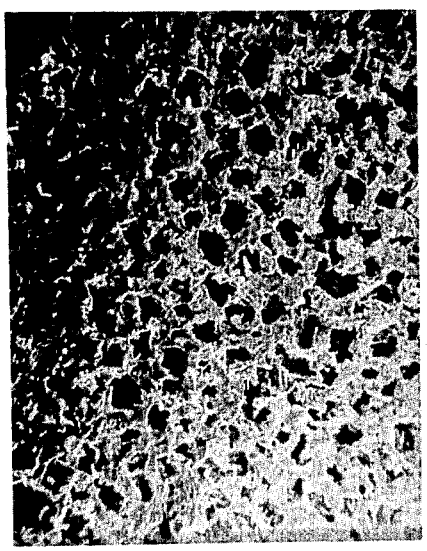
FIG. 7 is a photograph of a porous hydrophilic polyurethane element at 20 times magnification.
Figure 8:
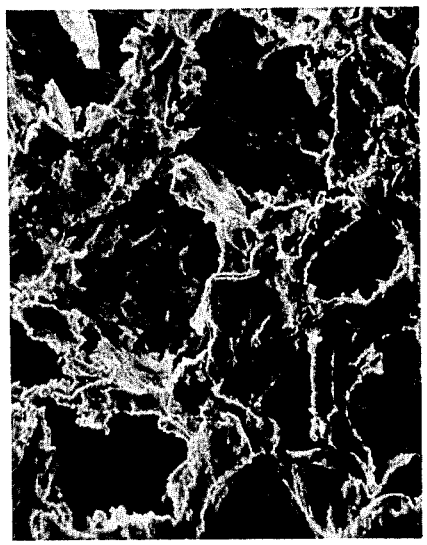
FIG. 8 is a photograph of the porous surface of FIG. 7 at 100 times magnification.

As may be seen in FIGS. 7 and 8, a flexible porous hydrophilic polyurethane product formed by the above procedure and using −200 +500 mesh sodium chloride particles, has an open porous structure in which the continuous polymer phase is irregularly shaped.

If desired, the totally porous product may be laminated in a mold or by solvent techniques with a solid coherent flexible polymer body.

Porous flexible polymeric materials have particular utility in the suture or sewing rings of heart valves. Suture rings often are formed of fabric filled with closed cell polymeric foam material. The porous flexible polymeric material having interconnected pores may be used as the polymeric filler of the suture ring.

Alternatively, the flexible porous polymeric material having interconnected pores may be provided as the outer surface of a conventional foam-filled fabric suture ring, either by direct attachment thereto or by attachment through an intermediate solid substrate.

A composite of a porous polymeric material and a solid coherent substrate may be utilized as the suture ring by direct secure attachment to the occluder seating ring. The attachment may be achieved by causing the solid substrate to flow into a porous metal surface of the character described in detail above on the seating ring and harden in the subsurface pores to interlock with the network of interconnected pores, for example, by pressure molding.

The latter procedure may be used, if desired, to provide flexible or rigid solid and/or porous plastic external coatings on rigid metal coatings on other heart valve components, by pressure molding a polymer to the metal coating.

In an alternate procedure for the formation of the flexible porous products, there may be first formed beads of polymer having a core of solvent-elutable material by solution coating of the core material. The beads then are compression molded to the desired shape and the product is leached to remove the solvent-elutable material to leave the porous material. The beads may be pressure molded to a solid polymer body, if desired, to provide a laminated structure after completion of the elution. Alternatively, the wholly porous product from the elution may be attached to a solid polymer body.

A further method of formation of the porous polymeric material is to form a casting solution of the polymer and solvent-elutable particles, cast the solution onto a casting surface, which may be a solid polymer substrate, if a composite structure is desired, and elute the solvent-elutable particles from the cast material.

Polymer coated solvent-elutable particles may be extruded to form tubes or the like when the device is to take this form. Following extrusion, or possibly molding, the tube is leached to remove the elutable particles. The tube may be provided in wholly porous form or may be formed as a laminate having a coherent solid polymeric substrate which has adhered inner and/or outer porous coatings. The laminate structures may be formed by lamination of the polymer coated solvent-elutable particle layers to the core layer prior to leaching. Alternatively, lamination may be carried out after leaching of the solvent-elutable particles from the polymer.

Tubular flexible polymeric materials which are wholly porous or have inner and/or outer porous surfaces adhered to coherent substrate are particularly useful as vascular grafts, particularly small diameter grafts of diameter less than about 6 mm.

Another procedure for the formation of a porous polymeric material is to cast the polymer around a lattice work which may then be rolled or formed into the desired shape.

Figure 9:
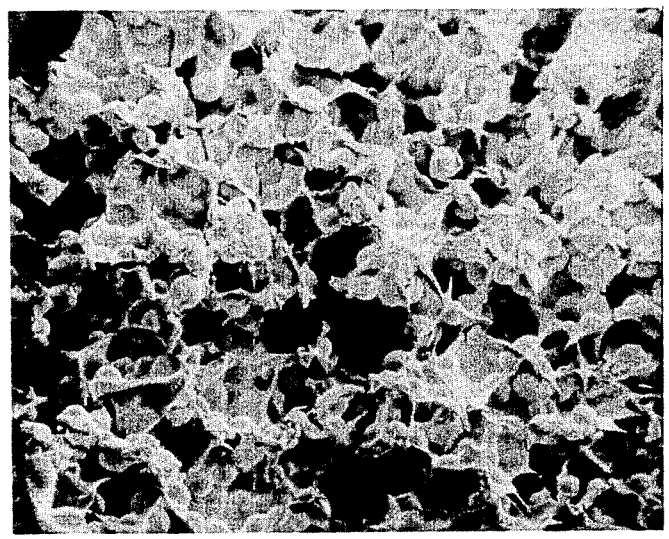
FIG. 9 is a photograph of a porous polymethylmethacrylate surface at 17 times magnification.
Figure 10:
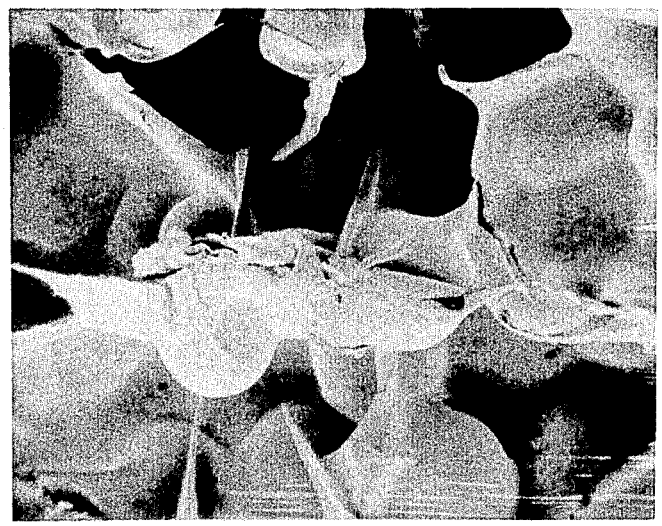
FIG. 10 is a photograph of the porous surface of FIG. 9 at 90 times magnification.

A further procedure for formation of a porous polymeric material involves providing a powdered solid polymer phase and a solvent phase including a solvent for the polymer. The liquid monomer phase is drawn rapidly through the powder particles so as to allow dissolving of polymer at the surface of the polymer particles only and to cause the formation of particle-toparticle joints. A typical rigid polymeric porous product formed in this way from polymethylmethacrylate particles of size −100 +325 mesh is shown in in FIGS. 9 and 10. The interconnection of the polymer particles and the porous nature of the product are clearly illustrated therein.

The wholly porous product formed in this latter procedure may be combined with a rigid polymeric member to form a composite structure, if desired.

The present invention may be used for a variety of cardiovascular applications in addition to those specifically mentioned above, including partially or totally implantable blood pumps, such as artificial hearts and ventricular assist devices, heart valve components, such as flexible flap-type valve members, other heart pacemaker electrode parts, rigid or flexible blood vessel grafts and patches, particularly small diameter grafts of diameter less than about 6 mm, blood stream filters, intracardiac patches, diaphragms or baffles and in vascular access tubes.

In the latter case, typically for use in haemodialysis, the inner surface of the tube is porous coated to promote colonization and tissue growth, while the outer surface also may be porous coated for soft tissue ingrowth.

In many applications of the present invention, the promotion of colonization and tissue growth is accompanied by true soft tissue ingrowth into the porous surface at the margins or on the outer surface from adjacent body tissue, to provide bonding between the host and the member, as described in my copending U.K. application Ser. No. 52474/75 filed Dec. 22, 1975.

The body tissue ingrowth combined with promotion of tissue growth on the porous surface from the nucleated blood stream cells is important in many applications of the present invention.

For example, in an artificial heart, a porous coating on all the elements provides a means of fixation to host tissues by soft tissue ingrowth and provides surfaces which are blood compatible arising from colonization and tissue formation on the blood-contacting surfaces.

The formation of the adherent tissue coating from nucleated blood cells also allows the cardiovascular prosthetic device or implant of the present invention to be incorporated into the cardiovascular system, thereby achieving a more secure attachment than has previously been the case.

The porous system interfacing blood in accordance with this invention in order to result in a tissue coating on the porous system also has other uses. Thus, non-cellular material may be sampled through the porous system, for detection of the presence and/or concentration of the constituents.

The interface between the circulating blood stream and an artifical endocrine organ may be porous. For example, an artifical pancreas may be provided in which glucose is sampled through a porous system interfacing with flowing blood and insulin and/or glucagon is released through the porous system and the tissue coating thereon interfacing with flowing blood. The source of the hormones and/or the control circuitry and/or the energy sources may be provided external to the body or may be implanted.

A slow release device interfacing blood may be provided, the device providing slow, sustained release of a substance into the blood through the porous system and its associated tissue coating interfacing the blood. The substance may be a drug, for example for long term antibiotic therapy, or hormones, for example, estrogens and/or progestigens providing a chronic implanted birth control device.

The parameters of the porous surface for use in the cardiovascular prosthetic devices and implants of this invention may vary widely and those chosen depend somewhat on the particular end use of the prosthetic device or implant. The surface must, however, have an interconnected network of pores underneath the surface in fluid flow communication with the surface pores to promote the colonization by nucleated cells and subsequent differentiation into other cell types so that the tissue which is formed and grows in the surface is interlocked in the subsurface network.

The interstitial surface pore size may vary widely, typically from about 1 micron up to about 1000 microns, although it may be preferred to use pore sizes below about 20 microns. As the pore size decreases, the surface becomes smoother, decreasing blood turbulence and abrasion on moving parts of the device.

The porosity also may vary widely, from about 8% upwards, although the porosity is usually in the range of about 10 to about 50%. Where a coating is provided on a coherent substrate, the thickness may vary from a single layer of particles upwards, for example, from about 1 to about 10,000 microns. Thin layers are preferred in devices having close tolerances.

EXAMPLES

The invention is illustrated by the following Examples:

EXAMPLE 1

Twenty-six prosthetic aortic ball valve cages were obtained and the poppets and sewing rings were removed. The metallic surfaces of fourteen of the cages were roughened, ultrasonically cleaned and coated with cobalt-base alloy powders (Vitallium) of various particle sizes to a depth of from about 100 to about 300 microns using the temperatures and times outlined in the following Table I:

TABLE I

| Powder Size | | No. of | | |
|---|---|---|---|---|
| Mesh | (μ) | cages | Temperature | Time |
| −500 | less than 20 | 2 | 2200° F (1200° C) | 1 hr |
| −325 +500 | 20 to 50 | 6 | 2330° F (1220° C) | 2½ hrs |
| −100 +325 | 50 to 200 | 6 | 2330° F (1220° C) | 2½ hrs |

The cages were implanted in the right atria of thirteen dogs, six of the dogs having implanted +500 mesh coated cages, one of the dogs having implanted the −500 mesh coated cages and the remaining six dogs having implanted uncoated cages as controls. The seating ring of each valve cage was fastened to the orifice of either the superior vena cava (SVC) or inferior vena cava (IVC) by an encircling umbilical tape such that the valve struts and their trifurcation were freely suspended in the right atrial cavity. No anticoagulants were given to any of the dogs.

One experimental dog and one control dog were sacrified at 2 weeks, 1 month, 6 weeks, 2 months, 3 months and 6 months after implantation. Upon removal, each valve cage was examined grossly for evidence of tissue growth as well as thrombus formation. The thrombus formation was graded on a scale of 0 to ++++, 0 representing a total absence of thrombus and + + + + representing total occlusion of the valve cage orifice by thrombus.

Additionally, the lungs were examined grossly for evidence of pulmonary embolism and representative sections of each lobe were taken for light microscopy.

At each time interval, one valve cage was examined by scanning electron microscopy and a special thin section of the other valve cage was prepared for transmitted and incident light microscopy using a low-speed diamond cut-off wheel. After the sections had been prepared, the tissue component was stained with a dilute solution of methylene blue.

The experimental dog containing the 2 valve cages with the −500 mesh powder-made metal surface was sacrified at 2 months. The tissue covering was torn of a portion of one of the valve struts and this area, as well as an area where the tissue covering remained intact, were examined by scanning electron microscopy. A special thin section was prepared from the second valve cage as described above, and is shown in FIG. 5.

All the porous-coated valve cages were found to have developed a thin, semi-transparent, smooth, firmly attached tissue covering with absolutely no evidence of thrombosis or embolism to the lungs. In most instances, the seating ring and base of the struts were totally incorporated into the walls of either the SVC or IVC at their points of attachment. In contrast, no tissue growth occurred on the uncoated valve struts and varying degrees of thrombus formation were observed in 10 of the 12 control valve cages. Additionally there was gross and microscopic evidence of pulmonary embolism in the control dogs sacrificed at 2 weeks, 6 weeks, and 3 months.

The results are reproduced in the following Table II:

TABLE II

| | Dog Number | Site | Particle Size (Microns) | Implant Time (months) | Thrombus Formation |
|---|---|---|---|---|---|
| Experimental | 1 | SVC | 50 to 200 | 0.5 | 0 |
| | | IVC | 20 to 50 | 0.5 | 0 |
| | 2 | SVC | 20 to 50 | 1.0 | 0 |
| | | IVC | 50 to 200 | 1.0 | 0 |
| | 3 | SVC | 50 to 200 | 1.5 | 0 |
| | | IVC | 20 to 50 | 1.5 | 0 |
| | 4 | SVC | 20 to 50 | 2.0 | 0 |
| | | IVC | 50 to 200 | 2.0 | 0 |
| | 5 | SVC | 50 to 200 | 3.0 | 0 |
| | | IVC | 20 to 50 | 3.0 | 0 |
| | 6 | SVC | 20 to 50 | 6.0 | 0 |
| | | IVC | 50 to 200 | 6.0 | 0 |
| Control | 7 | SVC | uncoated | 0.5 | +++ |
| | | IVC | uncoated | 0.5 | ++++ |
| | 8 | SVC | uncoated | 1.0 | 0 |
| | | IVC | uncoated | 1.0 | + |
| | 9 | SVC | uncoated | 1.5 | ++ |
| | | IVC | uncoated | 1.5 | + |
| | 10 | SVC | uncoated | 2.0 | + |
| | | IVC | uncoated | 2.0 | 0 |
| | 11 | SVC | uncoated | 3.0 | + |
| | | IVC | uncoated | 3.0 | ++ |
| | 12 | SVC | uncoated | 6.0 | ++ |
| | | IVC | uncoated | 6.0 | ++ |

Figure 6:
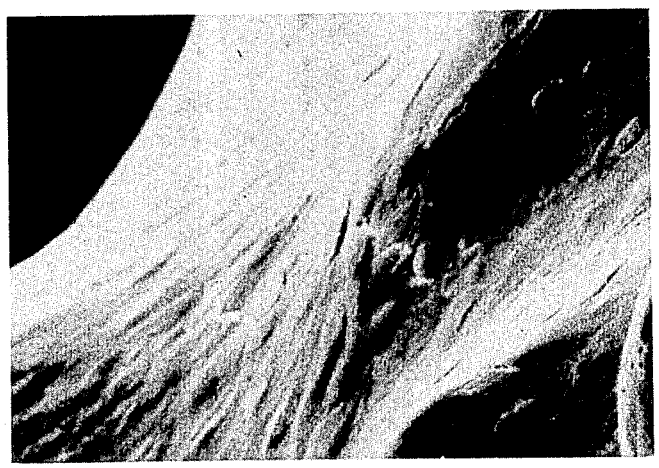
FIG. 6 is an electron micrograph of the tissue surface of composite porous coated metal body after positioning in the blood stream of a dog for 3 months at 700 times magnification showing endothelial cells in the tissue.

Scanning electron microscopy of the porous surfaces of the experimental valve cages showed a complete tissue covering as early as 2 weeks with the appearance of surface squamous endothelial cells at 3 months as illustrated in FIG. 6. The undulations in the tissue covering produced by the underlying spherical metal particles in both the coarse and medium powder-made surfaces were virtually eliminated by using the fine powder-made surface (particle size −500 mesh), as can be seen from FIG. 5.

Examination of the region in which the tissue covering was torn off the fine powder-made metal surface showed that the tissue had sheared off at the surface of the porous coating leaving fragments of tissue still affixed to the underlying pore structure.

Transmission light microscopy of the thin sections of the porous-coated struts showed the following evolution of the tissue covering. At 2 weeks the porous coating was covered with a material which resembles a platelet-fibrin mesh. Within this mesh were large mononuclear cells which have the ability to differentiate into other cell types. By 6 weeks, fibroblast-like cells had appeared and the porous coating was infiltrated and covered with connective tissue which was loosely textured within the porous coating and more compact towards the surface. Sections examined at 2 months showed well organized connective tissue within and over the surface of the porous coating. Pigment-filled macrophages had appeared and on the outer surface there were flattened endothelial-like cells. By 3 months, there was a uniform layer of connective tissue covering the entire surface of the porous metal coating which was quite compact even in its deeper layers. Again the surface was seen to be covered by flattened endothelial-like cells. Although some blood vessels were observed near the base of the struts where they had been in contact with the caval walls, no blood vessels were present in the tissue covering the struts which were freely suspended within the right atrial cavity. It would appear that the tissue growing on the valve struts was nourished by diffusion from the bloodstream and, as such, can survive without a blood vessel supply from the host.

Finally, the thickness of the tissue over and above the porous coating reached a maximum thickness of about 100μ which was independent of the underlying coating particle size.

EXAMPLE 2

A heart valve cage was coated with −325 +500 mesh Vitallium powder as described in Example 1 and was positioned in the descending thoracic aorta of a dog. After 6 months, the dog was still alive and well, indicating absence of major thromboembolism.

From a comparison of the results of Examples 1 and 2, it is apparent that the prevention of thromboembolism is independent of blood oxygen concentration and blood pressure.

EXAMPLE 3

A composite of a polymethyl methacrylate powder and a coherent polymethyl methacrylate base was mounted to the strut of a porous metal coated heart valve cage and placed in the right atrium of a dog. After 6 months, the dog was still alive and well, indicating probable endothelialization of the polymethyl methacrylate porous surface.

EXAMPLE 4

A 20% solution of a hydrophilic polyurethane consisting of urea interlinked blocks of polyether and chain extended urethane in dimethyl formamide and containing 4 g of polymer was slurried with 10 g of sodium chloride crystals of average size −200 +500 mesh. The slurry was dried in a vacuum oven to remove the solvent. The polymer coated salt was placed in a mold and compression molded at 300° to 350° F (150° to 175° C) for about 15 minutes. The mold was cooled and the sample removed.

After removal from the mold, the sample was immersed in a beaker of hot water and squeezed from time to time to assist in salt removal. After completion of the salt leaching, a porous spongy polymer product with interconnected pores resulted. The product had the microscopic appearance seen in FIGS. 7 and 8.

SUMMARY

The present invention, therefore, provides novel cardiovascular devices or implants which have biocompatibility and hence avoid the prior art thrombogenic problems. Modifications are possible within the scope of the invention.

What I claim is:

1. A heart valve structure comprising an occluder, an occluder seating ring and occluder guide means, each of said occluder seating ring and occluder guide means being constructed of metal inert to blood and consisting of a dense rigid, coherent metal substrate and a rigid porous metal coating adhered to at least a substantial portion of said substrate, said porous metal coating including a plurality of metal particles bonded together at their points of contact with each other and with said substrate to form a network of interconnected pores substantially uniformly distributed through the coating, said porous coating having a porosity of about 10 to about 50% and a thickness of about 20 to about 300 microns, said porous coating and the coating-substrate interface having a shear strength greater than about 1000 psi, the composite of said porous coating and substrate having a high fatigue tolerance, said metal particles having a particle size of −500 mesh.

2. The heart valve structure of claim 1 wherein said porous coating has a thickness of about 50 to about 150 microns, said shear strength is greater than about 3000 psi, and said composite has an endurance limit after $10^7$ cycles of greater than about 500 psi.

3. The heart valve structure of claim 1 including metal muscle guard means consisting of a dense rigid coherent metal substrate and said rigid porous metal coating adhered thereto.

4. The heart valve of claim 3 including a layer of polymeric material overlying and adhering to said porous metal coating on at least said occluder guide means, said layer of polymeric material comprising a dense coherent polymeric substrate interlocking with the interconnected pore network of the porous metal coating.

5. The heart valve of claim 4 wherein said polymeric substrate has an adhered porous polymeric coating having a plurality of interconnected pores therein.

6. A heart valve structure comprising an occluder, an occluder seating ring having sewing ring mounting means, occluder guide means, and a flexible sewing ring constructed of polymeric material inert to blood and body fluids and adhered to said sewing ring mounting means, each of said occluder seating ring and occluder guide means being constructed of metal inert to blood, at least a substantial proportion of each of occluder seating ring and occluder guide means consisting of a dense rigid coherent metal substrate and a rigid porous metal coating adhered to said substrate, said porous coating including a plurality of metal particles bonded together at their points of contact with each other and with said substrate to form a network of interconnected pores substantially uniformly distributed throughout said coating, said sewing ring comprising an outer layer of porous polymeric material having a plurality of interconnected pores distributed therethrough adhered to a flexible coherent polymeric substrate, said sewing ring being adhered to said sewing ring mounting means by interlock of said flexible coherent polymeric substrate in the interconnected pore network of the porous metal coating on said sewing ring mounting means.

* * * * *